(12) United States Patent
Schwager

(10) Patent No.: US 7,048,695 B1
(45) Date of Patent: May 23, 2006

(54) GUIDING AID

(75) Inventor: Michael Schwager, Winterthur (CH)

(73) Assignee: SciMed Life Systems, Inc., Maple Grove, MN (US)

( * ) Notice: Subject to any disclaimer, the term of this patent is extended or adjusted under 35 U.S.C. 154(b) by 186 days.

(21) Appl. No.: 10/070,939

(22) PCT Filed: Aug. 9, 2000

(86) PCT No.: PCT/EP00/07739

§ 371 (c)(1),
(2), (4) Date: May 13, 2002

(87) PCT Pub. No.: WO01/17601

PCT Pub. Date: Mar. 15, 2001

(30) Foreign Application Priority Data

Sep. 9, 1999 (EP) .................................. 99117818

(51) Int. Cl.
*A61B 5/00* (2006.01)
*A61M 25/00* (2006.01)
(52) U.S. Cl. ...................................... 600/585; 604/523
(58) Field of Classification Search ................ 600/585, 600/433–435; 604/264, 523
See application file for complete search history.

(56) References Cited

U.S. PATENT DOCUMENTS

| | | | |
|---|---|---|---|
| 4,846,186 A | 7/1989 | Box et al. | |
| 4,854,330 A | 8/1989 | Evans, III et al. | |
| 4,925,445 A | 5/1990 | Sakamoto et al. | |
| 5,040,543 A | 8/1991 | Badera et al. | |
| 5,637,089 A * | 6/1997 | Abrams et al. | 604/95.01 |
| 5,639,276 A | 6/1997 | Weinstock et al. | |
| 5,643,231 A * | 7/1997 | Lurie et al. | 604/532 |
| 5,680,873 A | 10/1997 | Berg et al. | |
| 5,722,963 A | 3/1998 | Lurie et al. | |
| 5,902,289 A * | 5/1999 | Swartz et al. | 604/530 |
| 6,090,084 A * | 7/2000 | Hassett et al. | 604/530 |
| 6,156,018 A * | 12/2000 | Hassett | 604/523 |
| 6,285,903 B1 * | 9/2001 | Rosenthal et al. | 600/433 |

FOREIGN PATENT DOCUMENTS

| | | |
|---|---|---|
| EP | 0 220 285 | 5/1987 |
| EP | 0 381 810 | 8/1990 |
| WO | WO 96/32980 | 10/1996 |
| WO | WO 97/32518 | 9/1997 |
| WO | WO 99/22797 | 5/1999 |

* cited by examiner

Primary Examiner—Charles Marmor
(74) Attorney, Agent, or Firm—Crompton, Seager & Tufte, LLC

(57) ABSTRACT

A guiding aid for an instrument to be advanced within a vascular system, particularly the human vascular system, comprising a flexible shapeable shaft comprising a first bent section having a first curvature and at least one further bent section, wherein the bent sections of the shaft have the same sign of curvature and are located substantially within the same plane. Such a guiding aid may be pre-formed by the manufacturer such that the guiding aid may be introduced into vascular branchings both from large lumen and small lumen vessels by a physician manipulating the instrument from its proximal end.

17 Claims, 3 Drawing Sheets

GUIDING AID

FIELD OF THE INVENTION

The invention relates to a guiding aid for an instrument to be advanced within a vascular system, particularly the human vascular system, comprising a flexible, formable shaft having a bent section with a predetermined curvature.

BACKGROUND OF THE INVENTION

Such guiding aids are used in transluminal interventions in the human vascular system where elongated instruments such as guide wires or catheters are manipulated at their proximal end by a physician to advance those instruments along a certain path through the vascular system to a site of treatment. For this purpose the instrument comprises at its distal end a tip which has approximately a J-shape and which either is pre-formed by the manufacturer or is individually bent by the physician. The column strength and the torsional strength of the instrument provide for axial and rotational movements being transferred from the proximal end of the instrument directly to the tip thereof. With the distal J-bow being correctly dimensioned the physician may navigate the instrument along a path selected by him through a branched vascular system such as the human blood vessel system.

From the prior art there are known various embodiments of instruments with such guiding aids. U.S. Pat. No. 4,846,186 discloses a flexible guide wire for advancing diagnostic and therapeutical catheters. The tapered core wire is flattened at its distal end such that it may be bent by the treating physician in this area into J-shape. A further application is shown in European Patent 0 220 285 wherein a balloon catheter is provided with a fixedly installed guide wire. The shaft of the wire which protrudes beyond the balloon is tapered and is surrounded by a wire helix. In the distal end section there is attached to the wire a shaped element made of stainless steel which in the relaxed state has a pre-selected curvature to serve as guiding aid. A guiding aid of the type mentioned above further is known from WO 97/32518; here there is provided a guide wire having a pressure measurement feature. At the distal end of the tubular wire there are located lateral openings through which a pressure pulse of the blood may propagate through the lumen of the tubular element to a pressure sensor located at the proximal end. A tip made of a formable shaft and a wire helix surrounding the shaft are provided at the distal end of the tubular element. Once the tips of the aforementioned embodiments are pre-formed the shape of the tip may not be changed any further during use thereof.

A guide wire having a tip the shape of which may be changed is known from U.S. Pat. No. 5,040,543. For this purpose the wire comprises an axially moveable core element the distal end of which may straighten the pre-curved helical wire tip. Thus the physician may control the size of the J-bow during the treatment from outside the patient. However, this construction is complicated and there is the risk, that the tip of the moveable core element may emerge between adjacent windings of the wire helix and may injure the inner wall of the vessel.

U.S. Pat. No. 4,925,445 discloses a guide wire for a catheter having a comparably stiff main section and a comparably flexible distal end section. These sections are made at least in part of a super elastic member. In order to prevent that the tip of the distal end section penetrates the wall of the vessel the tip is R-shaped, ball-shaped, J-shaped, annular or spiral. In order to be able to insert the distal end section in a simple and safe manner to a pre-selected position within the blood vessel, the distal end section is pre-formed by a curvature that corresponds to the anatomy of the vascular system or the vascular branching. This is disadvantageous in that for each individual intervention an individual shape of the guide wire tip has to be pre-manufactured which requires extensive storage.

SUMMARY OF THE INVENTION

It is therefore an object of the invention to provide for a guiding aid of the above mentioned type that is simple in construction and safe in application and which may be used for guiding elongated instruments in branchings of both large and small vessel diameters. This object is attained by a guiding aid of the above mentioned type, the shaft of which comprises at least one further bent section, wherein all bent sections of the shaft exhibit the same sign of curvature and are located substantially in the same plain. In large vessels the shaft, by means of the plurality of sections being bent in the same direction, may provide for sufficient total curvature such that the guiding aid may be threaded into a branching, optionally by bearing against a wall of the vessel opposite the branching. When being used in small vessels the further bent sections of the shaft proximal the first bent section of the guiding aid are straightened while the distal first bent section, when the curvature thereof is suitably dimensioned, maintains its shape to be maneuvered into a branching. Thus there is provided for an industrially pre-formable and thus standardized guiding aid that is suited for being threaded into branchings both from large and from small vessels. Furthermore, the physician no longer has to pre-form the shaft prior to the intervention himself.

In a preferred embodiment of the invention the shaft comprises just one further or second bent section having a further or second curvature that is located proximal of the first bent section such that the advantages of the invention are attained in a particular simple way by requiring that only two bent sections have to be pre-formed.

In a preferred embodiment of the invention the radius of curvature of the first bent section is smaller than the radius of curvature of the second bent section. Thereby the risk for buckling of the proximal curvature is lowered and the proximal curvature thereby is better adapted to transfer an axial movement to the distal curvature and the tip.

Preferably the shaft comprises between the first bent section and the second bent section a straight intermediate section in order to provide for an intermediate section that is stable for the transfer of axial movements which for example assists in preventing the distal end section of the guiding aid from again leaving a branching already entered by the distal end section.

In an advantageous embodiment of the invention the shaft comprises a straight end section to distal to the first bent section. This distal end section facilitates the entry into a branching by acting as support for the distal end of the shaft protruding into the branching.

In a preferred embodiment of the invention the straight end section and the straight intermediate section include a first obtuse angle and the straight intermediate section and the instrument axis include a second obtuse angle comprising an angle of in the range of from 120 to 150°, preferably of about 135°. As a result the straight end section is oriented laterally, for example under an angle in the order of about 90°, to the instrument axis in the direction of the opening of a branching and may be introduced into the branching particularly easily.

Advantageously the bent sections are substantially in the shape of a circular arc. This type of curvature is uniform and may be provided for with the most simple means.

In a further preferred embodiment of the invention the shaft is tapered towards its distal end, such that the shaft is more and more flexible towards its distal end. Thereby the risk of injury of the inner wall of the vessel by the tip of the shaft of the guiding aid is reduced.

In a further preferred embodiment of the invention there is provided around the shaft at least partially a helically wound spring. Thereby the risk for kinking of the wound shaft section is lowered while maintaining high flexibility. Furthermore, by means of the spring a rapid change of the outer diameter of the guiding aid is avoided in the tapered shaft. Preferably, the helically wound spring is provided at its distal end with a rounded terminal element to further lower the risk of injury.

In a further advantageous embodiment of the invention the shaft is comprised of a material with super elastic characteristics, preferably of super elastic Nitinol. Due to the shaft shape of the invention being adapted to be pre-shaped by the manufacturer this material having a shape memory effect may be used for the shaft.

In another preferred embodiment of the invention radio-paque means are provided in the region of the distal end of the shaft such that the instrument tip may be followed during navigation by the physician on an X-ray screen.

The invention relates further to the use of a guiding aid as described above with steerable instruments. In particular, the guiding aid of the invention may be located at the distal end for example of a guide wire, a pressure sensing wire or a balloon catheter. The practical attainment of the locating procedure or the attachment respectively of a guiding aid in or at such an instrument is known from the prior art described above such that these instruments may be provided with the inventive shape of the guiding aid and its advantageous use.

BRIEF DESCRIPTION OF THE DRAWINGS

Further advantages of the guiding aid of the invention will become apparent from the description of a preferred embodiment which will be described below by reference to the attached drawings wherein.

DETAILED DESCRIPTION OF THE INVENTION

Figure 1:
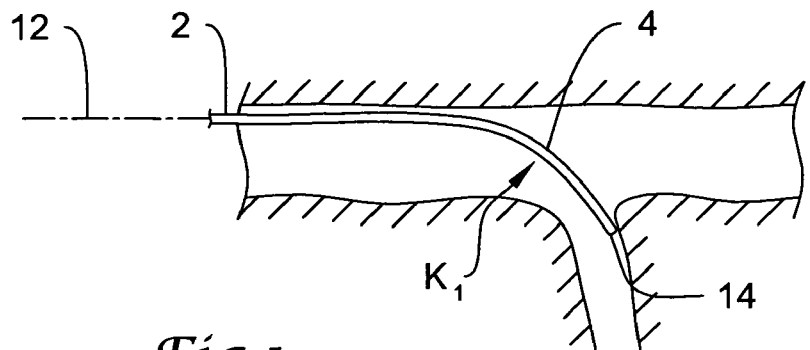
FIG. 1 shows a guiding aid comprising a J-shaped tip having the correct dimensions for the branching conditions.
Figure 2:
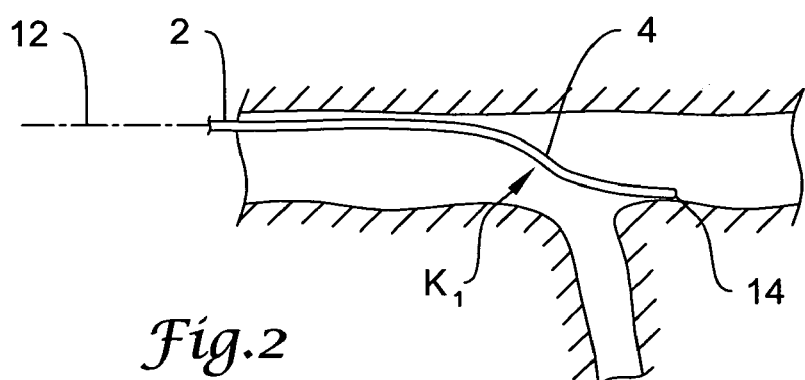
FIG. 2 illustrates a guiding aid with a J-shaped tip being dimensioned too large for the branching conditions.
Figure 3:
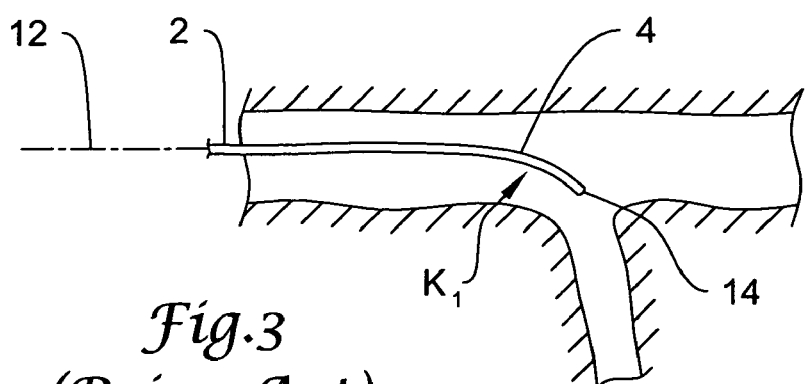
FIG. 3 illustrates a guiding aid with a J-shaped tip being dimensioned too small for the branching conditions.

A prior art guiding aid for an instrument to be advanced within the human vascular system having a flexible, shapeable shaft 2 comprising a first bent section 4 having a first curvature $K_1$ in J-shape is shown in FIGS. 1 to 3 in vascular branchings of different size. In FIG. 1 the curvature $K_1$ is dimensioned such that the distance of the distal end 14 of shaft 2 from the instrument axis 12 corresponds to about the diameter of the vessel from which the guiding aid is to be threaded into a branching. In this manner the tip of the guiding aid may protrude into the branching vessel even when the guiding aid bears proximally to the bent section 4 against the wall of the vessel opposite to the opening of the branching vessel. By rotating the instrument and thereby rotating the guiding aid about the instrument axis 12 the distal end 14 thereof is introduced into the branching easily and rapidly, provided the dimension of the bent section 4 corresponds to about the vessel diameter.

In FIG. 2 the curvature $K_1$ is dimensioned such that the distance of the distal end 14 from the instrument axis 12 is substantially larger than the diameter of the vessel from which the guiding aid is to be introduced into a branching. Within the small vessel the bent section 4 of the guiding aid is straightened such that the tip is directed substantially in the direction of the instrument axis 12. Therefore the tip of the guiding aid tends to pass the opening of the branching which renders the threading thereof into the branching difficult.

Threading of the guiding aid into a branching is similarly difficult in case that, as is shown in FIG. 3, the curvature $K_1$ is dimensioned such that the distance of the distal end 14 from the instrument axis 12 is substantially smaller than the diameter of the main vessel. Within the large lumen vessel there is no suitable lateral support for the guiding aid because when the shaft 2 bears against the wall of the vessel the distal end 14 of the guiding aid does not protrude into the vessel opening. This demonstrates to what an extent the successful advancement of an instrument with guiding aid is determined by the dimensioning of the curvature $K_1$ in relation to the size of the vessel diameter.

Figure 4:
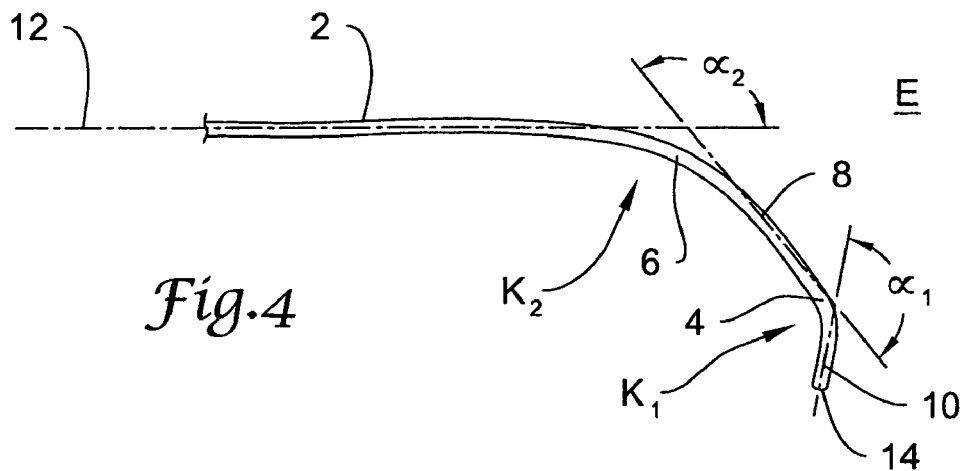
FIG. 4 is a schematic illustration of a guiding aid of the invention.

The guiding aid of the invention shown in FIG. 4 comprises a flexible shapeable shaft 2 having a first bent section 4 with a first curvature $K_1$ and proximal thereto a second bent section 6 with a second curvature $K_2$, wherein the two bent sections 4 and 6 of the shaft 2 exhibit the same sign of curvature and are positioned substantially in the same plane E which in FIG. 4 is the drawing plane. Shaft 2 comprises a straight intermediate section 8 between the bent sections 4 and 6 and a straight end section 10 distal to the first bent section 4 which end section 10 constitutes with its distal end 14 the tip of shaft 2. The straight intermediate section 8 and the straight end section 10 of the instrument include a first obtuse angle $\alpha_1$ and the straight intermediate section 8 and the axis 12 include a second obtuse angle $\alpha_2$. Bent sections 4 and 6 are substantially in the shape of a circular arc, with the radius of curvature of the first bent section 4 being smaller than the radius of curvature of the second bent section 6.

Figure 5:
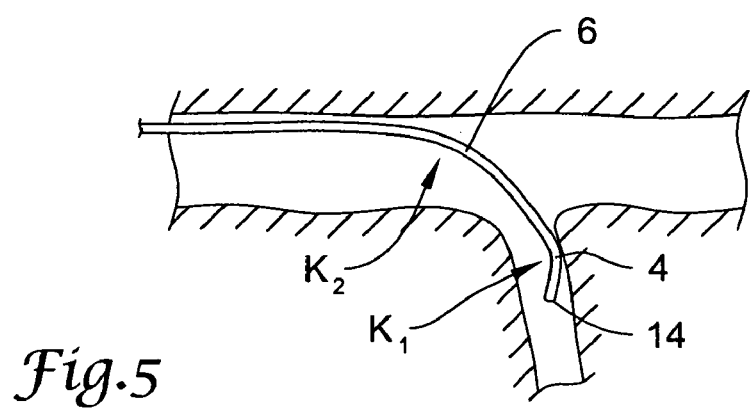
FIG. 5 shows the guiding aid of FIG. 4 at a branching from a large vessel.
Figure 6:
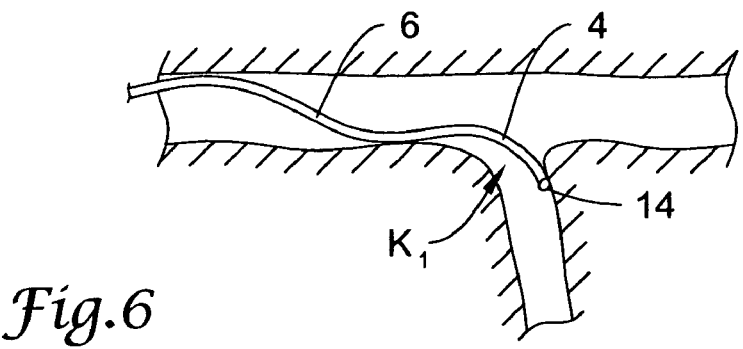
FIG. 6 shows the guiding aid of FIG. 4 at a branching from a small vessel.

In FIGS. 5 and 6 there is shown how the guiding aid of the invention is threaded from a large vessel and from a small vessel, respectively, into a branching. As is shown in FIG. 5 the curvatures $K_1$ and $K_2$ of the two bent sections 4 and 6, respectively, are dimensioned such that the tip 14 of the guiding aid protrudes into the opening of the branching even if the main vessel has a large lumen and even if shaft 2 bears against the wall of the main vessel opposite the opening of the branching. In case of a small lumen vessel, such as is shown in FIG. 6, although the proximal bent section 6 is straightened, the distal bent section 4 is dimensioned such that its curvature $K_1$ may be maintained and the tip 14 of the guiding aid may be introduced into the branching.

Figure 7:
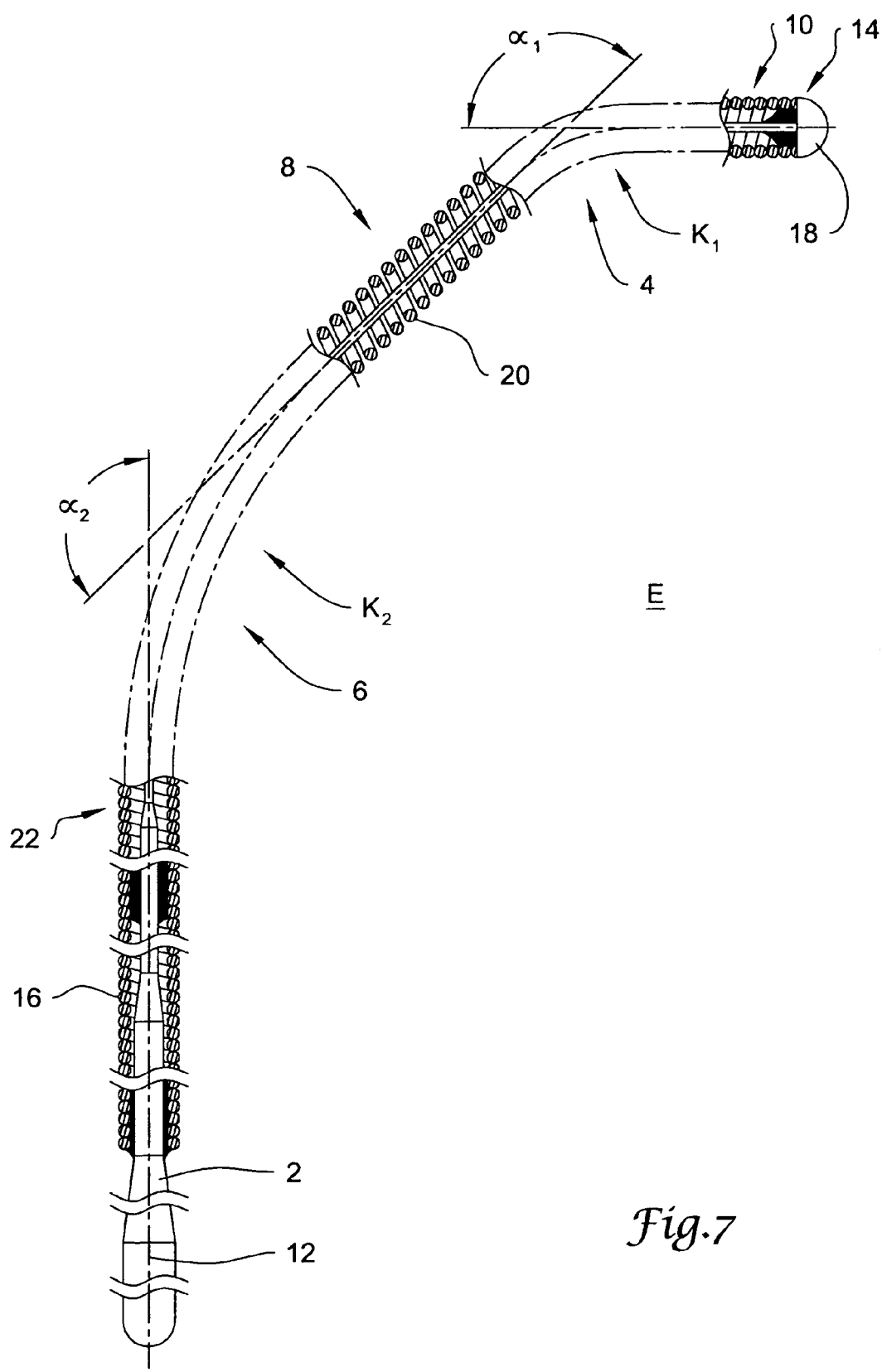
FIG. 7 shows a guide wire comprising a guiding aid of the invention in sectional view.

FIG. 7 shows a guide wire that is provided with a guiding aid of the invention. The flexible, shapeable shaft 2 of the guiding aid is constituted by the distal portion of the core wire of the guide wire, which, for coronary applications, has an outer diameter of typically about 0.35 mm. A first bent section 4 has a first curvature $K_1$, and proximal thereto a second bent section 6 has a second curvature $K_2$, with the two bent sections 4 and 6 being bent in the same direction with respect to the axis 12 of the instrument, i.e. with the same sign of curvature, and which are positioned substantially in the same plane E, which in FIG. 7 is the drawing plane. Between the bent sections 4 and 6 shaft 2 comprises a straight intermediate section 8 having a length of approximately 3 mm, and distal to the first bent section 4 shaft 2 comprises a straight end section 10 with a length of approximately 1.5 mm. The straight intermediate section 8 and the straight end section 10 of the instrument include a first obtuse angle $\alpha_1$, and the straight intermediate section 8 and the axis 12 include a second obtuse angle $\alpha_2$, with both obtuse angles having a value of about 135°. The bent sections 4 and 6 are formed substantially in the shape of a circular arc, with the radius of curvature of the first bent section 4 being about 3 mm and the radius of curvature of the second bent section 6 being about 8 mm. Shaft 2 is tapered toward its distal end 14 via a plurality of conical intermediate sections. In order to provide for a substantially constant outer diameter of the guide wire, a helical spring 16 is wound at least partially around shaft 2, preferably within the tapered shaft portion which within the region of the distal end 14 of the shaft 2 is made of a radiopaque material 20 which is threadedly connected to the proximal spring 16 at an attachment side 22 and/or is brazed or welded thereto. At the distal end 14 of the shaft 2 spring 20 is provided with a rounded terminal element 18, for example a solidified droplet of brazing metal. Spring 16 is attached to shaft 2 at its proximal end and preferably also at an additional location, for example by means of brazing or solder or adhesive connection. The core wire of the guide wire and thus shaft 2 preferably are made of Nitinol.

Although an embodiment of the invention having two bent or curved sections has been described above with reference to FIGS. 4 to 7, the guiding aid may comprise three or more bent or curved sections.

What is claimed is:

1. A guiding aid for an instrument to be advanced within a vascular system comprising:
    a flexible shapeable shaft including:
    a distal tip;
    a first bent section having a first curvature $K_1$;
    a second bent section proximal the first bent section, having a second curvature $K_2$, wherein the radius of the first curvature $K_1$ of said first bent section is smaller than the radius of the second curvature $K_2$ of said second bent section;
    a first axis extending from the distal tip of the guiding aid along a straight line in the direction in which the distal tip of the guiding aid is pointing;
    a straight intermediate section between the first and second bent sections, with a second axis along the straight intermediate section;
    a straight proximal section proximal the second bent section with a third axis along the straight proximal section; and
    an angle $\alpha_1$ between the first axis and the second axis and an angle $\alpha_2$ between the second axis and the third axis; with said bent sections of said shaft having the same sign of curvature and being located substantially in the same plane;
    wherein both $\alpha_1$ and $\alpha_2$ are obtuse angles.

2. The guiding aid of claim 1, wherein the shaft comprises a total of two bent sections.

3. The guiding aid of claim 1, further comprising a straight end section distal of the first bent section, wherein the first axis extends down the center of the straight end section.

4. The guiding aid of claim 1, wherein said first obtuse angle ($\alpha_1$) and second obtuse angle ($\alpha_2$) are between 120° and 150°.

5. The guiding aid of claim 1, wherein said bent sections are substantially in the shape of a circular arc.

6. The guiding aid of claim 1, wherein said shaft is tapered toward its distal end.

7. The guiding aid of claim 1, wherein a helically wound spring is located around at least a part of said shaft.

8. The guiding aid of claim 7, wherein said helically wound spring comprises a proximal and a distal end, wherein the distal end of the spring is provided with a rounded terminal element.

9. The guiding aid of claim 1, wherein said shaft is made of a material having superelastic characteristics.

10. The guiding aid of claim 9, wherein said shaft is made of superelastic nitinol.

11. The guiding aid of claim 1, wherein radiopaque means are provided in the region of said distal tip of said shaft.

12. The guiding aid of claim 1, wherein the total bend in the shaft is between 60° and 120°.

13. The guiding aid of claim 1, wherein the radius of the first curvature $K_1$ is about 3 mm and the radius of the second curvature $K_2$ is about 8 mm.

14. A guiding aid for an instrument to be advanced within a vascular system comprising:
    a flexible shapeable core wire;
    a distal tip;
    a first bent section having a first curvature $K_1$;
    a second bent section proximal the first bent section, having a second curvature $K_2$;
    a first axis extending from the distal tip of the guiding aid along a straight line in the direction in which the distal tip of the guiding aid is pointing;
    a straight intermediate section between the first and second bent sections, with a second axis along the straight intermediate section;
    a straight proximal section proximal the second bent section with a third axis along the straight proximal section; and
    an angle $\alpha_1$ between the first axis and the second axis and an angle $\alpha_2$ between the second axis and the third axis;
    wherein the radius of the first curvature $K_1$ is smaller than the radius of the second curvature $K_2$.

15. The guiding aid of claim 14, wherein both $\alpha_1$ and $\alpha_2$ are obtuse angles.

16. The guiding aid of claim 14, wherein the core wire comprises a material having superelastic characteristics.

17. A guiding aid for an instrument to be advanced within a vascular system comprising:
    a flexible shapeable shaft including a material having superelastic characteristics;
    a distal tip;
    a first bent section having a first curvature $K_1$;

a second bent section proximal the first bent section, having a second curvature $K_2$, wherein the radius of the first curvature $K_1$ of said first bent section is smaller than the radius of the second curvature $K_2$ of said second bent section;

a first axis extending from the distal tip of the guiding aid along a straight line in the direction in which the distal tip of the guiding aid is pointing;

a straight intermediate section between the first and second bent sections, with a second axis along the straight intermediate section;

a straight proximal section proximal the second bent section with a third axis along the straight proximal section; and an angle $\alpha_1$ between the first axis and the second axis and an angle $\alpha_2$ between the second axis and the third axis;

with said bent sections of said shaft having the same sign of curvature and being located substantially in the same plane;

wherein both $\alpha_1$ and $\alpha_2$ are obtuse angles.

* * * * *